United States Patent [19]

Hovis et al.

[11] Patent Number: 5,419,873
[45] Date of Patent: May 30, 1995

[54] APPARATUS FOR TRANSFER OF ACID CATALYST

[75] Inventors: Keith W. Hovis; Henry K. Hachmuth, both of Bartlesville, Okla.

[73] Assignee: Phillips Petroleum Company, Bartlesville, Okla.

[21] Appl. No.: 794,746

[22] Filed: Nov. 19, 1991

Related U.S. Application Data

[60] Continuation-in-part of Ser. No. 588,792, Sep. 27, 1990, abandoned, which is a division of Ser. No. 410,219, Sep. 21, 1989, Pat. No. 4,982,036.

[51] Int. Cl.⁶ .................................................. B01J 3/02
[52] U.S. Cl. .................................................. 422/113; 422/187
[58] Field of Search ............... 422/113, 187, 234, 235; 222/331, 399; 585/464, 723

[56] References Cited

U.S. PATENT DOCUMENTS

| | | | |
|---|---|---|---|
| 2,471,986 | 5/1949 | Waddill | 260/683.4 |
| 2,859,594 | 11/1958 | Peck | 62/50 |
| 2,992,078 | 7/1961 | Peters | 23/260 |
| 3,395,833 | 8/1968 | Rice, Jr. | 222/61 |
| 3,602,002 | 8/1971 | Bailey et al. | 62/53 |
| 4,110,996 | 9/1978 | Thompson | 62/54 |
| 4,348,544 | 9/1982 | Davis et al. | 585/300 |
| 4,409,420 | 10/1983 | Van Pool et al. | 585/723 |
| 4,861,560 | 8/1989 | Nakajima | 422/111 |
| 4,982,036 | 1/1991 | Hachmuth et al. | 585/723 |

Primary Examiner—Peter Kratz
Attorney, Agent, or Firm—George E. Bogatie

[57] ABSTRACT

Apparatus and a method are disclosed for transferring acid catalyst from a transport vehicle where liquid acid is carried under a relatively low vapor pressure level to a process vessel in an alkylation process where liquid acid is contained at a higher pressure level, while minimizing the loss of acid vapor to the environment. The acid transfer is accomplished without venting the process vessel by employing a relatively small volume pressure lock chamber between the transport vessel and the storage vessel. In a preferred embodiment the small volume pressure lock chamber also serves as a storage vessel for make-up acid which is added to the alkylation process as required.

9 Claims, 3 Drawing Sheets

APPARATUS FOR TRANSFER OF ACID CATALYST

This is a continuation-in-part of application Ser. No. 588,792, filed Sep. 27, 1990, now abandoned, which is a division of application Ser. No. 410,219, filed Sep. 21, 1989, now U.S. Pat. No. 4,982,036.

This invention relates generally to method and apparatus for handling fluids. In one aspect it relates to apparatus for fluid handling in an alkylation process. In another aspect it relates to a method for reducing loss of acidic material during transfer of acid catalyst from a transport vehicle to a process vessel in an alkylation process.

BACKGROUND OF THE INVENTION

It is common practice in the petroleum industry to produce high octane motor fuel by alkylating an isoparaffin with an olefin in the presence of a catalyst which preferably is liquid hydrofluoric acid or hydrogen fluoride (HF). Such a process is commonly known as an HF alkylation process or merely an alkylation process. The effluent from the alkylation reactor containing hydrocarbons and acid, is usually passed to a generally vertically arranged settler vessel at an intermediate point along the length of the settler vessel. A hydrocarbon phase is separated from an acid phase in the settler vessel, with the hydrocarbon phase contained in the upper part of the settler vessel and the acid phase contained in the lower part of the settler vessel. Accordingly a liquid-liquid interface between the acid phase and the hydrocarbon phase is formed within the settler vessel.

In a normal operation a portion of the liquid hydrofluoric acid phase is withdrawn from the lower part of the settler vessel, cooled and then recycled to the alkylation reactor for reuse in the alkylation process. It is known in an alkylation process that there is a tendency for water to accumulate in the acid catalyst as the acid catalyst is repeatedly recycled through the system. It is also known that a material known as acid soluble oil is produced in the alkylation reaction and that this material acts as diluent for the catalyst phase. In general the production of acid soluble oil is substantially in excess of that necessary or desirable for dilution of the catalyst.

It is common practice for alkylation systems employing acid type catalyst to include a so called "rerun" system through which at least a portion of the acid catalyst is continuously passed in normal operation to remove the water and the acid soluble oil. This purification of the acid catalyst results in anhydrous acid as a product and a small quantity of an azeotrope mixture of hydrogen fluoride and water as a by-product. The by-product mixture of hydrogen fluoride and water is generally discarded because of the relative difficulty accompanying it's separation.

Because of the loss of HF acid from the rerun systems as organically combined fluoride in the azeotrope mixture of water and hydrogen fluoride, make-up acid must be added to the alkylation catalyst system either continuously or at periodic intervals. In order to have available make-up hydrofluoric acid at all times, fresh anhydrous acid is stored in an HF acid storage vessel from which fresh acid is conveyed to the alkylation process when needed. The acid may be conveyed from the HF acid storage vessel directly to the reaction zone itself or to the settler vessel.

Even in HF acid alkylation systems where make-up acid is added occasionally, for example once a month, only about ten percent of the total volume of HF acid inventory used in the alkylation process is added for make-up at any one time. Thus the volume of time HF acid storage vessel required to handle the HF acid make-up would be approximately equal to the volume of ten percent of the total HF acid inventory required for tile alkylation process.

In order to safely operate the HF alkylation process, however, an acid inventory storage vessel of sufficient volume to contain the total inventor of HF acid used in the alkylation process must be provided. This storage space is necessary to provide a safe storage vessel where the total inventory of HF acid used throughout the process could be safely stored in the event of an emergency such as a leak somewhere in the process. The total acid inventory includes acid required in the reactor, the cooler, and the settler, plus approximately 10% excess for make-up storage. Since this acid inventory storage vessel is sized so as to hold the entire HF acid inventory but, under normal operation, only contains the quantity of acid required for make-up storage, there exists a relatively large vapor space in the acid inventory storage vessel under normal operating conditions. Transfer of make-up acid from the storage vessel to the alkylation process is usually accomplished by compressed gas. This transfer generally involves pressuring the relatively large vapor space in the storage vessel with a gas such as nitrogen so that liquid HF acid is transferred from the storage vessel to the alkylation process, which in operation is at about 100 to 150 psig pressure.

The fresh anhydrous liquid HF acid required to replenish the make-up acid, or provide an initial charge of acid catalyst, is usually transported in steel railroad tank cars or truck trailers to the plant where it is being used and stored, and the acid must be transferred from the tank cars or truck trailers where the liquid HF acid is under a vapor pressure of about 35–60 psig, to the HF acid alkylation storage vessel where a pressure of about 150–175 psig is required for transfer to the alkylation process.

Transfer of HF acid from the transport vehicle to the storage vessel is usually accomplished by isolating the storage vessel from alkylation process and then venting the pressure in the storage vessel while pressuring the transport vehicle with nitrogen gas in such a manner that the liquid acid is forced through a transfer line from the transport vehicle to the acid catalyst storage vessel at a relative low pressure level compatible with the transport vehicle.

In normal operation, the relatively large gas or vapor space above the liquid HF acid level in the HF acid inventory storage vessel is therefore filled with the pressuring gas required for transferring the acid catalyst to the alkylation process. Upon venting the storage vessel, such as at the time of replenishing the make-up acid, the vent gas carries with it a considerable amount of hydrogen fluoride which is then lost from the alkylation system. This loss of hydrogen fluoride, that may have vaporized under the conditions of temperature and pressure existing in the HF acid storage vessel, when replenishing the make-up acid constitutes not only an economic loss of valuable material but also introduces a potential environmental health hazard since neutralizing of such HF containing vapors may not always be 100 percent effective. It is desired, therefore, to eliminate or at least minimize the loss of hydrogen fluoride vapor with the gases vented from a storage vessel containing liquid hydrofluoric acid.

Accordingly it is an object of this invention to improve environmental safety in operating an HF alkylation process.

A further object of this invention is to increase the safety of a petroleum refining process and the apparatus employed therein.

Yet another object of this invention is to increase the efficiency of operation of an HF alkylation process.

Yet another object of this invention is to provide apparatus and method for reducing the loss of hydrofluoric acid vapors from a vessel in which make-up HF acid is stored and must be occasionally recharged.

SUMMARY OF THE INVENTION

In accordance with this invention, as applied to an alkylation process having an acid inventory storage vessel with capacity to contain the entire acid inventory of the alkylation process, a relatively small volume make-up catalyst storage vessel is temporarily connectable to the alkylation process in configurations for: (1) handling storage of make-up catalyst, and (2) effecting transfer of catalyst, using the acid make-up catalyst vessel as a pressure lock chamber, between a transport vehicle containing the acid catalyst at a reduced pressure level and the alkylation process containing catalyst at a higher pressure level. As used herein, a pressure lock chamber is an enclosure with gates on each end and which is useful for transferring material between a vessel at one pressure level to another vessel at another pressure level.

In a preferred embodiment, the make-up catalyst storage vessel has outlets and inlets for both liquid service and vapor service. For storing catalyst, a liquid outlet on the make-up catalyst vessel is temporarily connected to the acid inventory storage vessel or the settler vessel through a first shutoff valve, and a liquid inlet on the make-up catalyst vessel is blocked by a second shutoff valve. With this arrangement, liquid acid catalyst can be pressure transferred from the make-up storage vessel to the alkylation process. For transferring the liquid acid catalyst from the transport vehicle, the liquid outlet on the make-up storage vessel is blocked by the first shutoff valve and the liquid inlet is temporarily connected to the transport vehicle through the second shutoff valve. With this arrangement, liquid catalyst can be pressure transferred from the transport vehicle to the acid make-up storage vessel.

If desired, the initial charge of acid required for the alkylation process may be supplied directly to the big acid inventory storage vessel, and then pressure transferred to the settler vessel. Make-up acid can then be stored in the relatively small volume make-up storage vessel, and replacement make-up acid can be added to the make-up storage vessel directly from the transport vehicle, as required, without affecting the big acid inventory storage vessel. In this manner there is no need to pressurize the large vapor space in the acid inventory storage vessel to transfer make-up acid to the alkylation process. More importantly, there is no need to vent the large vapor space in the acid inventory storage vessel when transferring acid from a transport vehicle to replenish the make-up acid storage, thereby conserving the HF acid that may have vaporized in the inventory acid storage vessel.

Additional objects and advantages of the invention will be apparent from the following detailed description of the preferred embodiment of the invention as illustrated by the drawings in which:

DETAILED DESCRIPTION OF THE PREFERRED EMBODIMENT

Figure 1:
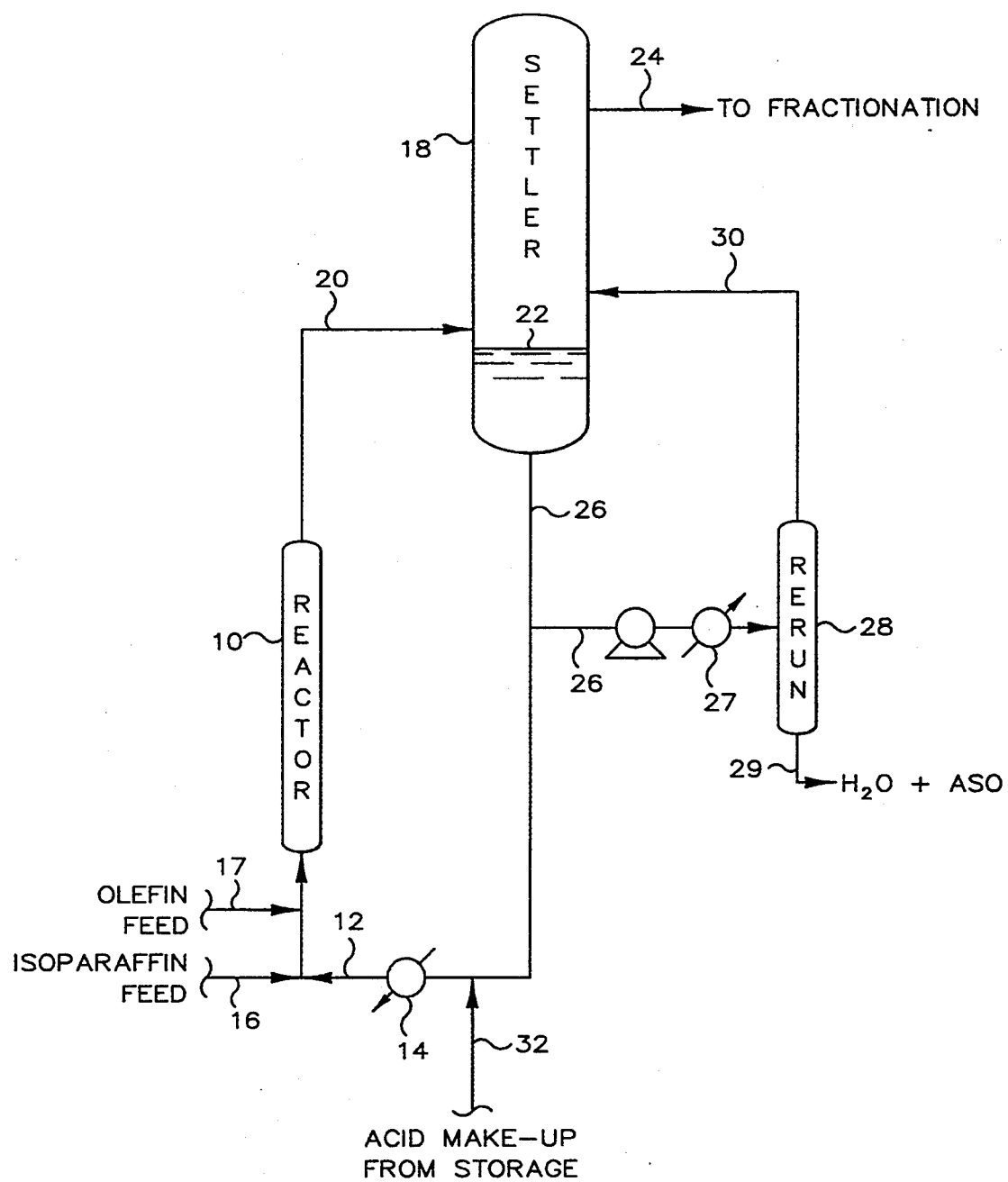
FIG. 1 is a schematic representation illustrating process flow of a simplified HF alkylation process.

The present invention can be employed in any of the catalytic refining processes in which make-up acid catalyst is required to replace the loss of acid catalyst, such as from an acid purification step which is typically employed for the removal of water and acid soluble oils present in the acid catalyst.

This invention is described in terms of an HF acid catalyst, however, a variety of alkylation catalysts can be employed in the alkylation process, including well known acid catalysts such as sulfuric acid, hydrofluoric acid, phosphoric acid, and other alkylation catalysts.

In the following discussion, parts which appear in more than one of the drawing figures shall be referred to by the same reference numeral in each of the drawing figures in which the part appears.

Referring now to the drawings, and in particular to FIG. 1, there is illustrated an alkylation reactor 10 which has inlet conduit 12 communicating therewith to supply liquid hydrofluoric acid. A cooler 14 is provided to cool the acid flowing in conduit 12. The feed stream of isoparaffins, such as isobutane, is supplied to the reactor 10 through conduit 16. An olefin feed stream, which can be a mixture of propylene and butylenes, for example, is supplied to the reactor 10 through conduit 17. The alkylation reaction is completed in reactor 10 by intimately contacting the hydrocarbons with the HF acid catalyst. The HF acid/hydrocarbon reaction mixture is removed from reactor 10 through a conduit 20 which communicates with a catalyst settler vessel 18.

In the catalyst settler vessel 18 the reaction effluent is separated into a hydrocarbon phase contained in the upper part of the catalyst settler vessel 18 and a catalyst phase contained in the lower part of the catalyst settler vessel 18. The combination of vessels including the reactor 10, cooler 14, and settler 18 contain an inventory of acid catalyst such that the level of acid catalyst 22 extends into the catalyst settler vessel 18.

The hydrocarbon phase contained in the upper part of the settler 18 is removed through a conduit 24 which communicates with a suitable separation means such as a fractionator, not illustrated. The acid phase in settler 18 is withdrawn through a conduit 26 which communicates with an acid purification unit 28. A portion of the acid withdrawn from the lower part of settler vessel 18 is heated in heater 27 and purified in acid purification unit 28 by distilling the acid from water and acid soluble oils. The purified acid is returned to the settler 18 through conduit 30 and the water and acid soluble oil is discharged through conduit 29. The remaining portion of the acid withdrawn from the lower part of settler vessel 18 is passed through conduit 12 to the cooler 14 and is recycled to the reactor 10. Make-up acid catalyst is supplied from a storage tank, as needed, through conduit 32 under compressed gas pressure.

Figure 2:
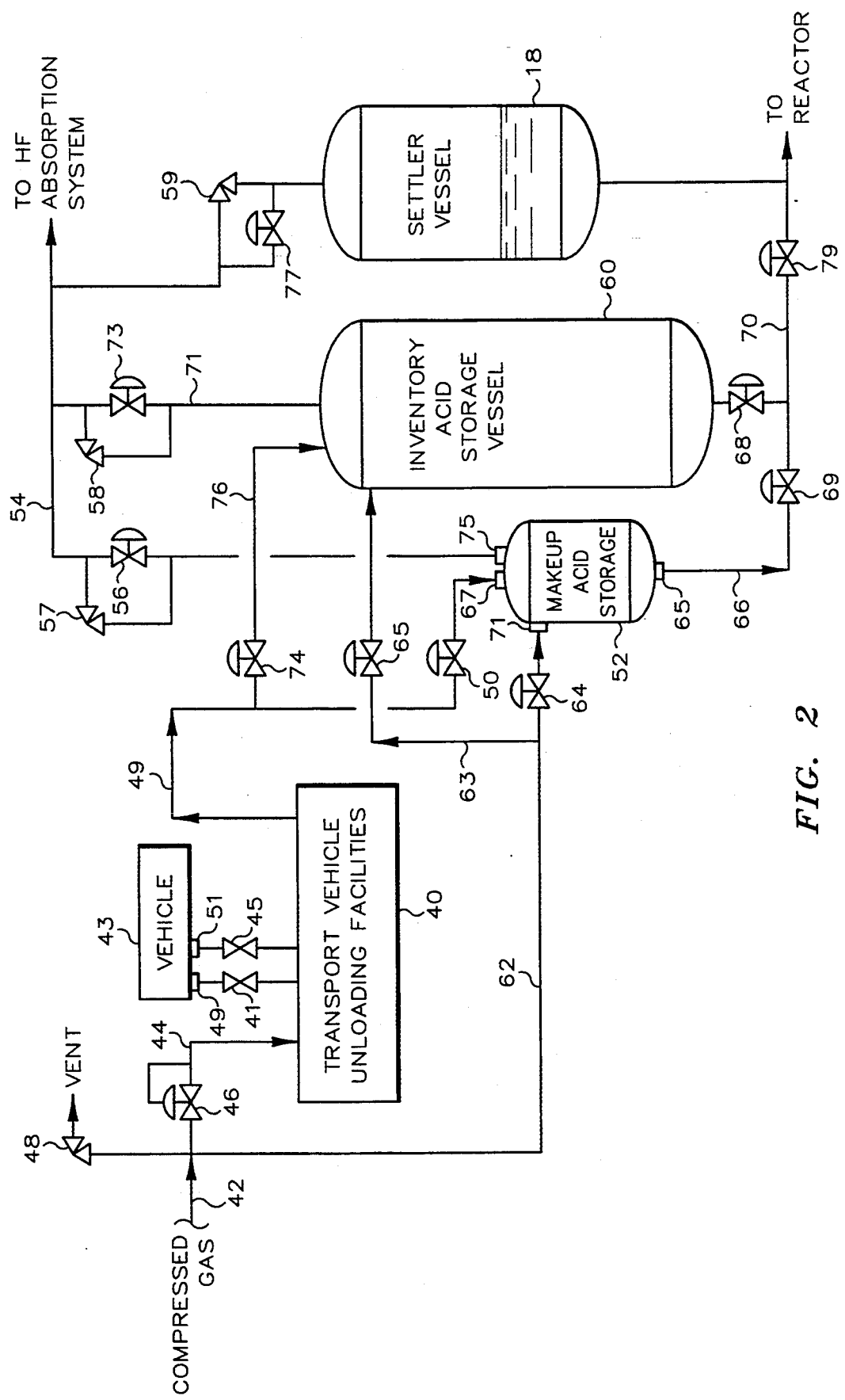
FIG. 2 is a schematic representation illustrating process flow of a compressed gas unloading system for a transport vehicle in accordance with the present invention.

Referring now to FIG. 2 there is illustrated a transport vehicle unloading facility 40 for a transport vehicle 43, such as a railroad tank car, or truck trailer having a valve arrangement including a safety relief valve (not illustrated) valve and valves for vapor service and liquid service. Compressed gas, usually nitrogen, at a pressure which does not exceed the relief valve setting of the transport vehicle is supplied to the transport vehicle inlet 47 via conduits 42, 44, pressure regulator valve 46 and the transport vehicle vapor service valve 41. A pressure relief valve 48, which communicates with the source of compressed gas supply via conduit 42, is also provided to insure that a safe pressure for the compressed gas will not be exceeded. Compressed gas is utilized to unload liquid HF acid catalyst contained in the transport vehicle 43 through the unloading facilities 40 via transport vehicle outlet 51 and liquid service valve 45 conduit 49 and valve 50 into a make-up catalyst storage vessel 52. The vessel 52 provides a relatively small volume for make-up storage compared to the acid inventory storage vessel 60. The vessel 52 is provided with liquid outlet 65, liquid inlet 67, vapor inlet 71 and vapor outlet 75, and is preferably temporarily connectable in parallel with the vessel 60, as illustrated in FIG. 2, via conduit 66 and of valves 68 and 69 at the bottom of the vessels and conduits 54 and 71 and valves 56 and 73 at the top of the vessels. Using the make-up storage vessel 52, acid may be added to the alkylation process from a transport vehicle 43 without venting the large vapor space of the inventory acid storage vessel 60 and thus avoiding the loss of HF acid vapor contained in the acid inventory vessel 60.

The compressed gas unloading procedure for the transport vehicle requires establishing a flow path from the transport vehicle 43 through the associated unloading facility 40 to the make-up catalyst storage vessel 52, and further requires equalizing the pressures in the transport vehicle 43 and the vessel 52. Equalizing the pressure may be accomplished by isolating vessel 52 from the alkylation process by closing valves 68, 69, 73, 74 and 77 and then venting the vessel 52 through an HF absorption system via conduit 54 and valve 56. After transfer of the liquid acid catalyst from the transport vehicle to the make-up acid storage vessel 52, the vessel 52 is then isolated from the transport vehicle 43 before being pressurized to transfer the liquid HF acid to the alkylation process. Compressed gas, supplied via conduit 62 and valve 64 to the vapor inlet 71, is utilized to transfer the liquid HF acid contained in the vessel 52 into the alkylation process through valves 69 and 79 wherein the vessel 52 is pressurized to a pressure level which does not exceed the setting of pressure relief valve 57, 58, or 59. Transfer of the HF acid from liquid outlet 65 of the acid make-up storage vessel 52 to the alkylation process vessel which comprises the inventory acid storage vessel 60 and the reactor is accomplished by establishing a flow of HF acid via conduit 66 and valves 69, and 79. Further compressed gas supplied to the acid inventory storage vessel 60 via conduits 62 and 63, and valve 65 can be utilized to provide an initial catalyst charge to the process or to add HF acid catalyst to the alkylation process via conduit 70 and valves 68 and 79 if desired. Also illustrated in FIG. 2 is valve 74 and conduit 76 which may be utilized for supplying an initial charge of HF acid catalyst to the inventory storage vessel 60 from the transport vehicle, as well as conduit 71 and valve 73 which may be utilized to vent the inventory acid storage vessel 60 while supplying acid catalyst to vessel 60 via conduit 76.

Figure 3:
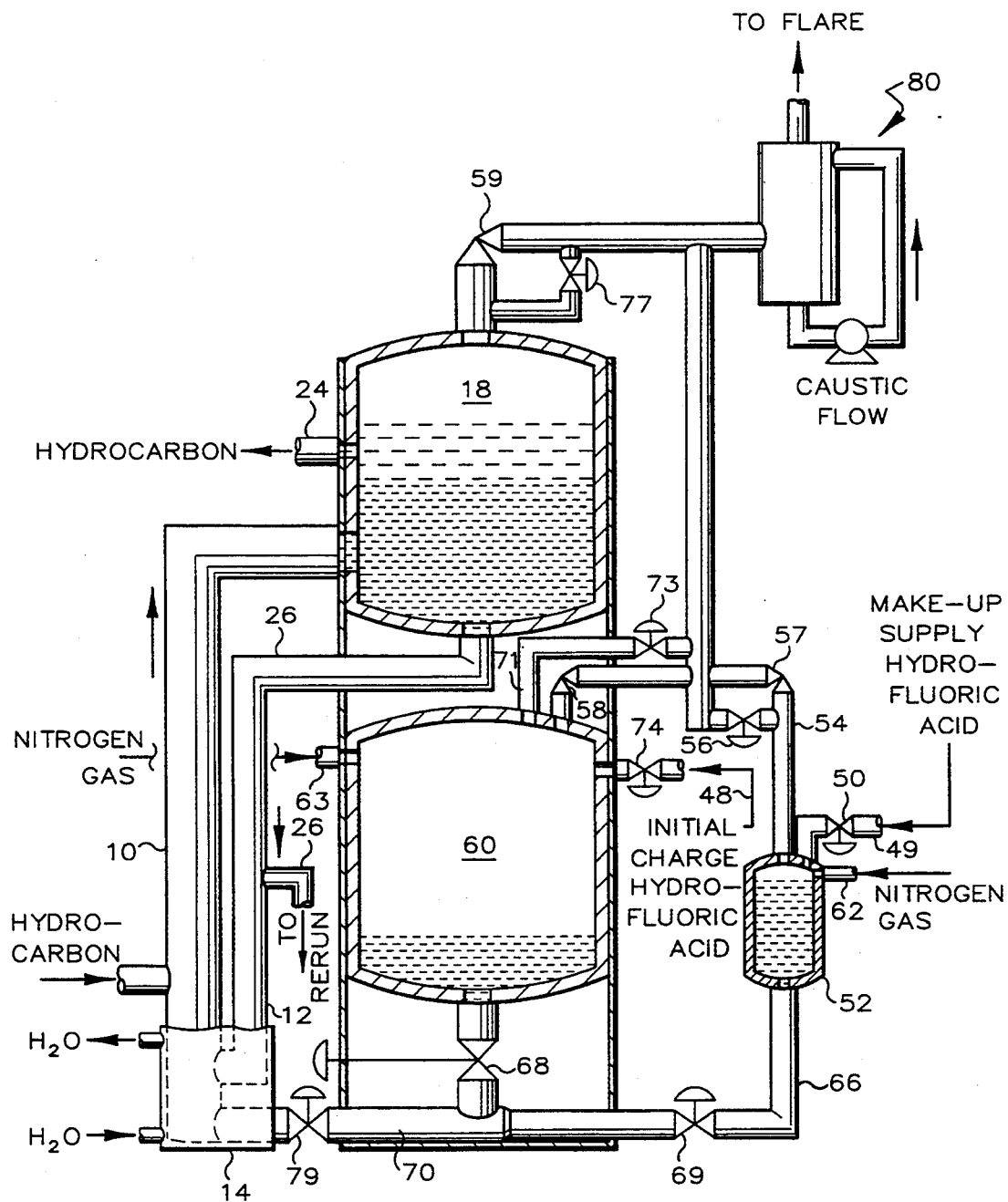
FIG. 3 is an elevation view, partly in section, of a riser reactor, a settler vessel, a acid make-up storage vessel, an acid inventory acid storage vessel and an acid cooler illustrated in an arrangement suitable for carrying out this invention.

Referring now to FIG. 3 there is illustrated an arrangement of process vessels which is suitable for use in the present invention. The illustrated reaction system maintains high circulation of HF acid through the acid cooler 14 by means of differential gravity between liquids in the two legs 10 and 12 associated with cooler 14. Further illustrated in FIG. 3 is the HF absorption system generally indicated at 80 in which hydrogen fluoride is absorbed from waste gas prior to flaring the waste gas, and valve 79 which connects the inventory storage vessel 60 to the reactor 10.

This invention is applicable to various transport vehicles such as railroad tank cars, truck trailers, etc. which transport HF acid to user facilities. In accordance with the invention, the process apparatus includes a large acid inventory storage vessel and a relatively small acid make-up storage vessel. Loss of acid vapor is minimized in the alkylation process by storing the make-up acid in the relatively small acid storage vessel 52, and further minimized by using the make-up acid storage vessel 52 as a pressure lock chamber in transferring acid catalyst to the alkylation process from a transport vehicle.

Various modifications of this invention can be made in view of the foregoing disclosure and the appended claims without departing from the spirit and scope of this invention and therefore such variations and modifications are within the scope of the present invention as claimed.

That which is claimed is:

1. Apparatus for transferring a liquid acid catalyst from a transport vehicle containing said catalyst at a first pressure level to an alkylation process employing a settler vessel containing said catalyst at a second pressure level, said apparatus comprising:
   (a) an acid inventory storage vessel for containing said catalyst at said second pressure level, said acid inventory storage vessel being connectable by conduit to said settler vessel in said alkylation process;
   (b) said acid inventory storage vessel being of sufficient volume for containing substantially the total quantity of said catalyst used in said alkylation process;
   (c) a make-up catalyst storage vessel having a liquid inlet and outlet, and a vapor inlet and outlet, said liquid outlet of said make-up catalyst storage vessel being temporarily connectable to said settler vessel and said liquid inlet being temporarily connectable by conduit to said transport vehicle;
   (d) said make-up storage vessel having a volume substantially less than the volume of said inventory storage vessel for storing a quantity of make-up catalyst substantially less than the total quantity of catalyst used in said alkylation process; and
   (e) means, utilizing said make-up acid storage vessel as a pressure lock chamber, for transferring said catalyst from said transport vehicle to said settler vessel.

2. An apparatus for transferring a liquid acid catalyst in an alkylation process, said apparatus comprising:

process vessel means associated with said alkylation process for containing said liquid acid catalyst at a first pressure level;

a make-up acid catalyst storage vessel associated with said alkylation process, said make-up acid catalyst storage vessel having a liquid inlet and outlet and a vapor inlet and outlet, and having a volume substantially less than the volume of said process vessel means;

first conduit means for connecting said liquid outlet on said make-up acid storage vessel to an inlet on said process vessel means;

unloading means for a transport vehicle containing liquid acid catalyst under vapor pressure at a second pressure level, said transport vehicle having an inlet and an outlet;

second conduit means for connecting said liquid inlet on said make-up acid storage vessel to said outlet of said transport vehicle; and transfer means, utilizing said make-up acid catalyst storage means as a pressure lock chamber, for passing liquid acid catalyst from said transport vehicle containing liquid acid catalyst at said second pressure level to said process vessel means containing liquid acid catalyst at said first pressure level.

3. Apparatus in accordance with claim 2, wherein said unloading means comprises:

source of compressed gas;

third conduit means for connecting said source of compressed gas to said inlet on said transport vehicle; and wherein said compressed gas sufficiently pressures the transport vehicle to facilitate transfer of said liquid acid catalyst contained in the transport vehicle.

4. Apparatus in accordance with claim 2, wherein said transfer means comprises:

a first shutoff valve operably located for controlling flow in said second conduit means;

means for venting said make-up acid catalyst storage vessel while receiving liquid acid catalyst through said second conduit means;

means for flowing liquid acid catalyst through said first conduit means; and second shutoff valve operably located for controlling flow in said first conduit means.

5. Apparatus in accordance with claim 4, wherein said means or flowing liquid acid catalyst through said first conduit means comprises;

a compressed gas source;

fourth conduit means for connecting a source of compessed gas to said vapor inlet of said make-up acid catalyst storage vessel; and wherein said source of compressed gas sufficiently pressures said make-up acid catalyst storage vessel to facilitate transfer of said liquid acid catalyst contained in sand make-up acid catalyst storage vessel.

6. Apparatus in accordance with claim 5, wherein said means for venting said make-up acid catalyst storage vessel comprises:

fifth conduit means for venting said vapor outlet on said make-up acid catalyst storage vessel; and a third shutoff valve operatively located in said fifth conduit means for controlling venting of said make-up acid storage vessel.

7. Apparatus in accordance with claim 2 wherein said process vessel is a settler vessel associated with an alkylation process.

8. Apparatus in accordance with claim 2 wherein said process vessel is an alyklation reactor.

9. Apparatus in accordance with claim 2 wherein said first pressure level is greater than said second pressure level.

* * * * *